United States Patent
Matyushin et al.

(10) Patent No.: US 6,224,764 B1
(45) Date of Patent: May 1, 2001

(54) APPARATUS FOR PURIFYING AND DISINFECTING WATER

(75) Inventors: Gennady Alexeevich Matyushin; Zoya Kirillovna Kim, both of Moscow (RU)

(73) Assignee: R-Amtech International, Inc., Bellevue, WA (US)

( * ) Notice: Subject to any disclaimer, the term of this patent is extended or adjusted under 35 U.S.C. 154(b) by 0 days.

(21) Appl. No.: 09/310,200

(22) Filed: May 12, 1999

Related U.S. Application Data

(63) Continuation-in-part of application No. 08/912,527, filed on Aug. 18, 1997, now abandoned.

(30) Foreign Application Priority Data

Aug. 19, 1996 (DE) ............................................. 196 33 352

(51) Int. Cl.⁷ ................................................. B01D 24/08
(52) U.S. Cl. ......................... 210/266; 210/283; 210/289; 210/352; 210/502.1
(58) Field of Search ................................. 210/266, 282, 210/283, 284, 290, 289, 352, 502.1; 239/33

(56) References Cited

U.S. PATENT DOCUMENTS

| | | | |
|---|---|---|---|
| 3,389,803 | * 6/1968 | Barley | 210/282 |
| 3,680,707 | * 8/1972 | Zeek | 210/266 |
| 4,039,452 | * 8/1977 | Fernandez | 210/106 |
| 4,298,475 | 11/1981 | Gartner | 210/266 |
| 4,826,594 | * 5/1989 | Sedman | 210/282 |
| 4,995,976 | * 2/1991 | Vemes et al. | 210/266 |
| 5,273,649 | * 12/1993 | Magnusson et al. | 210/232 |
| 5,456,831 | * 10/1995 | Sullivan | 210/266 |
| 5,509,605 | * 4/1996 | Cripe | 210/266 |
| 5,518,613 | * 5/1996 | Koczur et al. | 210/266 |
| 5,545,315 | * 8/1996 | Lonneman | 210/266 |

* cited by examiner

*Primary Examiner*—David A. Simmons
*Assistant Examiner*—Frank M. Lawrence
(74) *Attorney, Agent, or Firm*—Rothwell, Figg, Ernst & Manbeck

(57) ABSTRACT

An apparatus for purifying and disinfecting water including a tubular housing having a rear inlet end and a front outlet end, a disinfection stage and an absorption stage containing activated charcoal being provided in the housing between the rear inlet end and the front outlet end. Each of the disinfection stage and the absorption stage have a front end and a rear end at which a respective perforated cylindrical insert is arranged, the cylindrical inserts having an outside diameter which corresponds substantially to the inside diameter of the housing. The inserts at the front and the rear end of the disinfection stage and the insert at the front end of the absorption stage are arranged to be stationary and the insert at the rear end of the absorption stage is arranged to be axially displaceable. A spring element which exerts a pressing force on the insert at the rear end of the absorption stage in the direction toward the absorption stage is provided in the tubular housing between the insert at the front end of the disinfection stage and the insert at the rear end of the absorption stage.

7 Claims, 1 Drawing Sheet

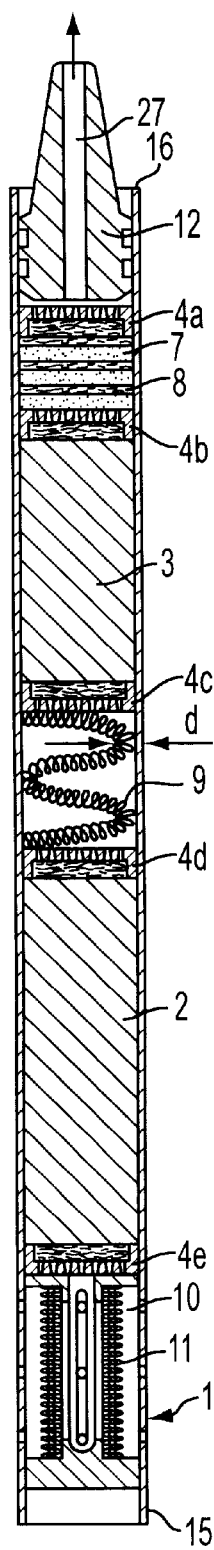
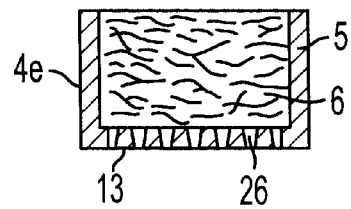
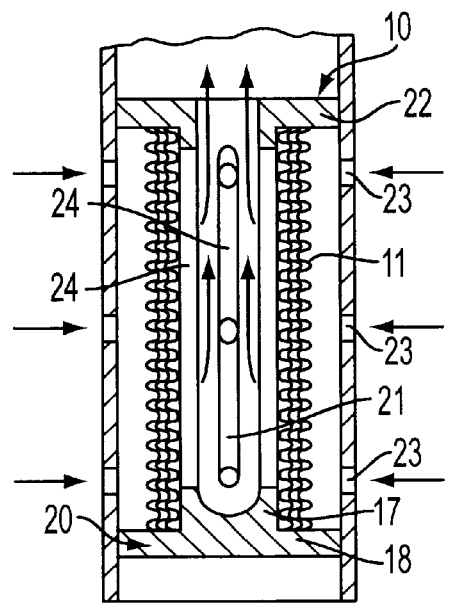
FIG. 1
FIG. 2
FIG. 3

APPARATUS FOR PURIFYING AND DISINFECTING WATER

This application is a continuation-in-part application of U.S. Ser. No. 08/912,527 filed Aug. 18, 1997, now abandoned.

BACKGROUND OF THE INVENTION

1. Field of the Invention

The present invention is in the water purifying and disinfecting field.

2. Description of the Background Art

U.S. Pat. No. 4,298,475 discloses an apparatus of which the tubular plastics housing accommodates an inlet-end stage of porous material, a further stage having a polyhalide anion exchange resin layer, an intermediate filter of porous polymer, an outlet filter of porous polymer and a mouthpiece. Owing to this construction, sewage water is sufficiently disinfected from microorganisms and mechanical impurities are removed to a certain extent. If, using the known apparatus, for example, river water having an initial enteric bacteria contamination of $10^5$ microbe cells/liter and having a content of mechanical impurities of from 60 to 100 mg/liter is sucked up continuously, the water leaving the outlet end has a contamination of enteric bacteria of from 10 to 100 microbe cells/liter and a content of mechanical impurities of from 40 to 70 mg/liter.

Those values are inadequate. In addition, the amount of water that can flow through the housing is small when the water contains a large amount of impurities of organic and inorganic origin. The average amount of water which can be taken up using such an apparatus is not more than from 10 to 15 l. The known apparatus must then be discarded.

U.S. Pat. No. 4,995,976 discloses an apparatus having a tubular housing of polycarbonate in the case of which the inlet-end stage is formed by an inlet filter which is produced from porous plastics material having a pore size of 80 μm and which is placed on the inlet end of the housing. A purification stage which is formed by a purifying resin and which is used to kill bacteria, organic materials and organisms adjoins the inlet-end stage. The next stage contains activated charcoal for absorption. Finally, a sterilisation stage is provided. The individual stages are separated from one another by porous spacer discs. A respective layer of resilient foam having a larger pore size than the inlet filter or the spacer discs is provided on the front and the rear end of the activated charcoal layer.

This apparatus is able to provide purification and disinfection of water improved by one order of magnitude compared with the apparatus known from U.S. Pat. No. 4,298,475. The total amount of water which can be purified using this apparatus is, however, not greater.

SUMMARY OF THE INVENTION

The problem of the invention is to provide, using constructionally simple means, an apparatus for purifying and disinfecting water by means of which it is possible to purify and disinfect adequately a large amount of water.

That problem is solved by an apparatus for purifying and disinfecting water including a tubular housing comprising a rear inlet end and a front outlet end, a disinfection stage and an absorption stage containing activated charcoal being provided in said housing between said rear inlet end and said front outlet end, each of said disinfection stage and said absorption stage having a front end and a rear end at which a respective perforated cylindrical insert is arranged, said cylindrical inserts having an outside diameter which corresponds substantially to the inside diameter of said housing, said inserts at said front and said rear end of said disinfection stage and said insert at said front end of said absorption stage being arranged to be stationary and said insert at said rear end of said absorption stage being arranged to be axially displaceable, a spring element exerts a pressing force on said insert at said rear end of said absorption stage in the direction towards said absorption stage being provided in the tubular housing between said insert at said front end of said disinfection stage and said insert at said rear end of said absorption stage.

The apparatus according to the invention ensures adequate disinfection of bacteria, viruses and bacteriophages regardless of the initial contamination of the water. The resilient force of the spring element moves the insert at the rear end of the absorption stage in the direction of insert at the front end of the disinfection stage when the volume of the adsorption stage increases due to adsorbed substances. Therefore both, formation of ducts in the adsorption stage through which the water could flow without sufficient absorption and clogging of the absorption stage is prevented. Further the spring element creates turbulences in the space between the absorption and the disinfection stage. This involves an improved mixing and a longer residence time of the solved iodine in the water which leads to a more effective disinfection.

BRIEF DESCRIPTION OF THE DRAWINGS

An embodiment of the invention is described in more detail hereinafter with reference to drawings, in which:

FIG. 1 is a longitudinal section through an apparatus for purifying and disinfecting water;

FIG. 2 is a longitudinal section through a perforated insert; and

FIG. 3 is a longitudinal section through the inlet-end stage of the apparatus of FIG. 1 on an enlarged scale.

DETAILED DESCRIPTION OF THE INVENTION

The apparatus shown in FIG. 1 for purifying and disinfecting water has a cylindrical tubular housing 1 of polymer having an inlet end 15 and an outlet end 16. Several stages for purification, disinfection and sterilisation are provided in the housing 1.

A filter stage 10 which is shown in more detail in FIG. 3 is arranged at the inlet end 15 of the housing 1. The filter stage 10 comprises a spool-form carrier element 10 having an upper flange 22 and a lower flange 18 of which the outside diameters correspond substantially to the inside diameter of the housing 1. The two flanges 18, 22 are connected to one another by an elongate cylindrical connecting portion 17 which is arranged coaxially with the housing 1. A coaxially extending duct 21 which leads into the front surface of the front flange 22 is formed in the connecting portion 17. The duct 21 is closed at its lower end in the vicinity of the lower flange. Several (four in the Example shown) longitudinal slots 24 which are distributed at an equal distance from one another around the circumference of the connecting portion 17 are provided in the side wall of the connecting portion 17. The longitudinal slots 24 lead into the duct 21 and into the outer face of the connecting portion 17.

A filter material 11 formed from fibres containing activated charcoal is arranged around the connecting portion 17.

For the entry of water, several distributed through-openings 23 which ensure that a sufficient amount of water can enter radially into the filter stage 10 are provided in the wall of the housing 1 at the level of the connecting portion.

Owing to the fact that the lower flange 18 is connected sealingly to the housing 1 and does not have any through-openings, axial entry of water into the housing 1 is prevented.

The through-bores 23 are distributed evenly around the circumference of the housing 1. In the Example shown, three respective through-openings are arranged opposite one longitudinal slot 24. The size, number and arrangement of the through-bores can, however, vary as long as a sufficient amount of water flows radially into the filter stage 10.

A cylindrical-pot-shaped insert 4e which is shown enlarged in FIG. 2 adjoins the filter stage 10. The insert 4e has a base 13 which is provided with several evenly distributed through-openings 26. The space between the cylinder wall 5 and the base 13 of the insert 4e is filled with fibre material 6 containing activated charcoal. The outside diameter of the insert 4e corresponds to the inside diameter of the housing 1. The insert 4e is placed with its base 13 on the front flange 22 of the filter stage 10.

A disinfection stage 2, which comprises, for example, disinfecting ion-exchanging resin with which the housing 1 is filled in this region, is arranged adjacent to the side of the insert 4e remote from the filter stage 10. The disinfection stage 2 is delimited at its front end by a further insert 4d which is constructed in exactly the same manner as the insert 4e, the base of the insert 4d being remote from the disinfection stage 2.

A further identically constructed insert 4c is arranged at a distance from the insert 4d in such a manner that its base faces the base of the insert 4d. The insert 4c is arranged to be axially displaceable in the housing 1, while the insert 4d is arranged to be stationary, that is to say, it is non-displaceable. A helical compression spring 9 which is composed of wound fibre material containing activated charcoal or of wound polymer is arranged in the space of the housing 1 between the bases of the inserts 4c and 4d. The spring element 9 exerts a forwardly directed pressing force on the insert 4c.

The material of the spring element 9 has a porosity of 4 cm³/g. As it is shown in FIG. 1, the outer diameter of the spring element 9 is equal to the inner diameter of the tubular housing 1. The thickness d of the spring element is 4±1 mm.

An absorption stage 3 containing activated charcoal with which the housing 1 is filled in this region is provided above the insert 4c. The absorption stage 3 is delimited at its front end by a further non-displaceably arranged insert 4b which is constructed in the same manner as the insert 4e, the base of the insert 4b being remote from the absorption stage 3.

A sterilisation stage is provided upstream of the insert 4b. The sterilisation stage has three layers 7 of sterilising material between which an intermediate layer 8 of fibre material containing activated charcoal is provided. A further insert 4a which likewise corresponds to the insert 4e is arranged adjacent to the sterilisation stage 7, the base of the insert 4a being remote from the sterilisation stage.

A mouthpiece 12 which has an axially extending through-duct 27 and which is inserted into the outlet end 16 of the housing 1 adjoins the insert 4a.

The height of the filter stage 10 is approximately from 10 to 12% of the height of the housing 1. The ratio of the height of the disinfection stage to the height of the absorption stage is from 5:4 to 2:1. A polyhalide anion exchange resin or another resin having analogous bacteria-killing properties may be used as the material for the disinfection stage. The polyhalide may be iodine, bromine or a combination thereof. It is also possible to use five or more intermediate layers of fibre material containing activated charcoal.

In order to take up water, the apparatus according to the invention is held with its inlet end 15 in a contaminated water source. A partial vacuum is created at the mouthpiece 12. The water passes through the through-bores 23 in the wall of the housing 1 and into the space between the carrier element 20 and the wall of the housing 1 and flows substantially radially through the filter material 11 of fibre material containing activated charcoal and through the longitudinal slots 24 into the duct 21 of the connecting portion 17. Mechanical impurities are removed from the water by means of the filter material 11.

The water then flows through the disinfection stage 2, the insert 4d, the insert 4c and the absorption stage 3 of activated charcoal in which substances dissolved in the water are absorbed. Here the taste of the purified water is improved and, in addition, the content of any remaining iodine or the like in the water is reduced. The compression spring 9 exerts pressure on the absorption stage 3 by way of the insert 4c. The resilient force of the spring element 9 is determined such that the insert 4c can move in the direction of insert 4d when the volume of the adsorption stage 3 increases due to the adsorbed substances. Therefore both, formation of ducts in the adsorption stage 3 through which the water could flow without sufficient absorption and clogging of the absorption stage 3 is prevented.

After the absorption stage 3, the water flows through the layers 7 of sterilising material and the intermediate layers 8 of material containing activated charcoal, the water being normalised by the layers 8. Furthermore, additional filtering and absorption of substances dissolved in the water is effected by the intermediate layers 8. The degree of purification increases with the number of intermediate layers of activated charcoal fibre material.

Finally, the water enters the mouthpiece 12 from where it can be used.

During use iodine is washed out from the ion-exchanging resin in the disinfection stage 2 and the remaining resin swells and its volume increases. As the inserts 4e and 4d are fixed the swelling of the resin and the increase of the volume leads to a compression of the resin to such extent that the waterflow through the disinfection stage 2 is stopped. This completely prevents water from being drunk with the apparatus when the iodine in the disinfection stage 2 is exhausted.

The apparatus according to the invention was tested for its throughput capacity, its purifying ability in respect of toxic organic and mechanical impurities, its disinfecting action, water throughput through the apparatus and content of disinfecting material in the purified water.

The expression "throughput capacity" is intended to mean the volumetric flow which takes place through the apparatus until the throughput through the apparatus is three times lower than the initial throughput. The disinfecting action is determined with reference to the content of enteric bacteria in the purified water. According to the Russian Federation standard GOST 2874-82, water of which the content of enteric bacteria is greater than three microbe cells/liter is unsuitable for drinking. The degree of purification of the water in respect of mechanical contamination is the ratio of the impurities in the purified water to the impurities in the incoming water. The flow throughput through the apparatus is the amount of water (in ml) which flows through the apparatus in one minute when there is a pressure difference of 0.2 atm between the inlet end and the outlet end. If a polyiodine anion exchange resin is used as the disinfecting material, the content of disinfecting material in the purified water is determined with reference to the content of iodine in the purified water. If the content of iodine is greater than 4 mg/liter, the water has a bad odour and is unsuitable for drinking. The degree of purification of the water in respect of toxic organic impurities is determined by the percentage ratio of the concentration of those impurities in the water before and after passage through the apparatus.

In a test carried out on the apparatus according to the invention, a pump created a partial vacuum of 0.2 atm. 0.5 l of river water per day was sucked through the apparatus in order to determine the volumetric flow that could be achieved through the apparatus.

The river water had an initial contamination with enteric bacteria of $10^5$ microbe cells/liter and a degree of contamination with mechanical impurities of 60 mg/liter.

The housing had a length of 200 mm and an inside diameter of 10 mm. The height of the filter stage 10 was 25 mm, or 12.5% of the length of the housing 1. The ratio of the height of the disinfecting layer 2 of polyiodine resin SIA-1 (TU 64-2-381-87) to the height of the absorption layer 3 with activated lignin charcoal was 3:2. Silver-containing cation-exchanging material having a silver ion content of 8.5 mg/liter with a grain size of from 0.5 to 1.2 mm was used as the sterilising agent. The height of the sterilisation stage was 10 mm or 5% of the length of the housing.

A throughput capacity of 25 l was achieved with this apparatus. The content of enteric bacteria in the purified water was less than 3 microbe cells/liter. A degree of purification for mechanical impurities of 10% was achieved. The throughput of water through the apparatus was 125 ml/minute. The iodine content of the water leaving the apparatus was 2.5 mg/liter.

What is claimed is:

1. An apparatus for purifying and disinfecting water including a tubular housing having an inside diameter and including a rear inlet end and a front outlet end, a disinfection stage and an absorption stage containing activated charcoal being provided in said housing between said rear inlet end and said front outlet end, each of said disinfection stage and said absorption stage having a front end and a rear end at which a respective perforated cylindrical insert is arranged, said cylindrical inserts having an outside diameter which corresponds substantially to the inside diameter of said housing, said inserts at said front and said rear end of said disinfection stage and said insert at said front end of said absorption stage being arranged to be stationary and said insert at said rear end of said absorption stage being arranged to be axially displaceable, a spring element which exerts a pressing force on said insert at said rear end of said absorption stage in a direction toward said absorption stage being provided in the tubular housing between said insert at said front end of said disinfection stage and said insert at said rear end of said absorption stage, wherein said inserts are pot-shaped and have a porous base which is remote from the associated stage, fibers containing activated charcoal being arranged between said base and the corresponding stage.

2. The apparatus according to claim 1, wherein said spring element comprises wound material containing activated charcoal.

3. The apparatus according to claim 1, wherein said spring element is made of a fibrous carbon-containing material having a porosity of 0.4 cm$^3$/g.

4. The apparatus according to claim 1, wherein said spring element has a thickness of 4±1 mm.

5. The apparatus according to claim 1, wherein said spring element has a diameter which is equal to said inner diameter of said tubular housing.

6. An apparatus for purifying and disinfecting water including a tubular housing comprising a rear inlet end and a front outlet end, a disinfection stage and an absorption stage containing activated charcoal being provided in said housing between said rear inlet end and said front outlet end, each of said disinfection stage and said absorption stage having a front end and a rear end at which a respective perforated cylindrical insert is arranged, said cylindrical inserts having an outside diameter which corresponds substantially to the inside diameter of said housing, said inserts at said front and said rear end of said disinfection stage and said insert at said front end of said absorption stage being arranged to be stationary and said insert at said rear end of said absorption stage being arranged to be axially displaceable, a spring element which exerts a pressing force on said insert at said rear end of said absorption stage in the direction towards said absorption stage being provided in the housing between said insert at said front end of said disinfection stage and said insert at said rear end of said absorption stage, said spring element comprising wound material containing activated charcoal.

7. An apparatus for purifying and disinfecting water including a tubular housing comprising a rear inlet end and a front outlet end, a disinfection stage and an absorption stage containing activated charcoal being provided in said housing between said rear inlet end and said front outlet end, each of said disinfection stage and said absorption stage having a front end and a rear end at which a respective perforated cylindrical insert is arranged, said cylindrical inserts having an outside diameter which corresponds substantially to the inside diameter of said housing, said inserts at said front and said rear end of said disinfection stage and said insert at said front end of said absorption stage being arranged to be stationary and said insert at said rear end of said absorption stage being arranged to be axially displaceable, a spring element which exerts a pressing force on said insert at said rear end of said absorption stage in the direction towards said absorption stage being provided in the housing between said insert at said front end of said disinfection stage and said insert at said rear end of said absorption stage, said spring element comprising wound fibrous carbon-containing material having a porosity of 0.4 cm$^3$/g.

* * * * *